United States Patent [19]

Friese et al.

[11] Patent Number: 4,741,738
[45] Date of Patent: May 3, 1988

[54] SULFONATION OF FATS AND OILS

[75] Inventors: Hans-Herbert Friese, Monheim; Friedrich Pieper, Langenfeld, both of Fed. Rep. of Germany

[73] Assignee: Henkel Kommanditgesellschaft auf Aktien, Duesseldorf, Fed. Rep. of Germany

[21] Appl. No.: 53,573

[22] Filed: May 21, 1987

Related U.S. Application Data

[63] Continuation of Ser. No. 785,430, Oct. 8, 1985, abandoned.

[30] Foreign Application Priority Data

Oct. 12, 1984 [DE] Fed. Rep. of Germany ....... 3437443

[51] Int. Cl.$^4$ ...................... C14C 3/00; C07C 143/90
[52] U.S. Cl. .................................. 8/94.19 R; 8/94.22; 8/94.23; 260/400; 260/686
[58] Field of Search ................. 260/400, 686; 8/94.19, 8/94.22, 94.23

[56] References Cited

U.S. PATENT DOCUMENTS 2,210,140  8/1940  Colbeth ................................. 252/56
3,300,525  1/1967  Plapper et al. ...................... 260/400

FOREIGN PATENT DOCUMENTS 0989669  4/1965  United Kingdom .

OTHER PUBLICATIONS

"Webster's New World Dictionary," World Publishing Company, New York (1968), p. 1159.

Primary Examiner—Charles F. Warren
Assistant Examiner—Elizabeth A. Hanley
Attorney, Agent, or Firm—Ernest G. Szoke; Henry E. Millson, Jr.; Mark A. Greenfield

[57] ABSTRACT

A process for the sulfonation of certain fat and oil mixtures, the product of such process, and a method for using such product as a leather tanning stuffing agent, the certain fat and oil mixtures comprising (A) 20–80% by weight of at least one $C_{8-24}$-fatty acid glycerol ester having an iodine number above 20, and (B) the balance q.s. to 100% by weight of at least one $C_{1-4}$-aliphatic monoalcohol ester of a $C_{8-24}$-fatty acid having an iodine number of 50–100.

25 Claims, No Drawings

SULFONATION OF FATS AND OILS

This application is a continuation of application Ser. No. 785,430, filed Oct. 8, 1985, now abandoned.

BACKGROUND OF THE INVENTION

1. Field of the Invention

This invention relates to an improved process for the sulfonation of unsaturated fats and oils and the use of the sulfonated products in leather manufacture.

2. Statement of the Related Art

Stuffing agents for the manufacture of leather and skins are produced, inter alia, by the introduction of sulfonate and/or sulfate groups into unsaturated oils and fats. This gives water-soluble or water-emulsifiable compounds which are used in the fat-liquoring bath, optionally together with other standard auxiliaries such as emulsifiers or non-sulfonated oils.

Products of this type may be obtained by the reaction of fats containing unsaturated fractions with sulfuric acid, fuming sulfuric acid (oleum), or $SO_3$, although in those cases—particularly where $SO_3$ is used—dark-colored products are formed which are then bleached, unless sulfonation is carried out in the presence of large quantities of an inert solvent. To obtain substantially pure products of low neutralizing-agent-produced-salt content, sulfonation may also be carried out with a mixture of $SO_3$ and air or inert gas although, in that instance, subsequent bleaching is again necessary (see British patent No. 989,669 and corresponding published German patent application No. 12 46 717).

The above-described difficulties in the sulfonation of fats containing unsaturated fractions are partly attributable to the fact that there is a considerable increase in viscosity during the reaction due to the formation of sulfonic acids or sulfuric acid esters. This impedes the further reaction, resulting in long contact times between the fats and the sulfonating agent and in dark colorations and carbonization. In addition, the increase in viscosity greatly reduces throughput in the apparatus used. In particular, the sulfonation reaction with a mixture of $SO_3$ and air in falling-film or cascade reactors is seriously impeded by the increase in viscosity because it greatly reduces the rate of flow in the thin liquid layers, possibly resulting in complete blockage of the reactor. If the reaction is carried out at low temperatures, further difficulties arise through inhomogeneities in the fats.

DESCRIPTION OF THE INVENTION

The present invention provides an improvement over the known sulfonation process carried out with a mixture of $SO_3$ and air. Accordingly, the present invention provides a process for the production of an agent suitable for stuffing (plumping) leather and skins, by sulfonation of fats and oils containing unsaturated fractions with sulfuric acid, oleum or $SO_3$, followed by neutralization and, optionally, by bleaching, wherein as an improvement, a mixture of (A) from 20 to 80% by weight of at least one $C_{8-24}$ fatty acid glycerol ester having an iodine number above 20 and (B) the balance q.s. to 100% by weight of at least one $C_{1-4}$ aliphatic monoalcohol ester of a $C_{8-24}$ fatty acid which fatty acid is liquid at room temperature and which ester has an iodine number of from 50 to 100, is subjected to sulfonation.

The claimed mixture improves the homogeneity of the fats and, more particularly, reduces the viscosity of the sulfonation products. This provides for better control of the reaction, for higher throughputs through the apparatus used, for more defined degrees of sulfonation, and for the formation of homogeneous, clear sulfonation products of good color quality. There is no need for the fatty acid ester added to be removed after sulfonation because it is also sulfonated and, as a neutral oil fraction, contributes to the effectiveness of the stuffing agent. If very light end products are required, the sulfonation products may readily be bleached with $H_2O_2$ without any adverse effects upon the other advantageous properties of the products. In addition, the homogeneity and low viscosity of the sulfonation products enable the stuffing agent to be used without difficulty and to penetrate more readily into the leather.

Fats useful as component (A) include: natural or synthetic higher $C_{8-24}$, preferably $C_{16-24}$ triglycerides having average iodine numbers of above 20, preferably 50 to 200, more particularly natural fatty acid triglyceride mixtures or fatty acid triglyceride mixtures produced from natural vegetable or animal fats: which fatty acids are partly mono- or poly-unsaturated. Examples of component (A) include: lard oil, neat's-foot oil, fish oil, rape seed oil, peanut oil, olive oil and their mixtures. Component (A) preferably comprises 50 to 70% by weight of the mixture with component (B).

The alcohol component of the component (B) $C_{8-24}$, preferably $C_{12-20}$, fatty acid esters may be an aliphatic $C_{1-4}$ (preferably $C_{1-3}$) monoalcohol such as, methanol, ethanol, isopropanol, isobutanol or their mixtures. The esters should be liquid and homogeneous at room temperature, i.e. should have melting points below 20° C. It is preferred to use $C_{12-20}$ fatty acid ester mixtures having iodine numbers of from 60 to 80, the alcohol component of the ester being methyl and/or ethyl. Examples of component (B) include: a $C_{12-18}$ fatty acid methyl ester having an iodine number of 60 to 70; a $C_{16-18}$ fatty acid ethyl ester having an iodine number of 60 to 70; a $C_{10-20}$ fatty acid methyl ester with an iodine number of 65 to 75; a $C_{12-20}$ fatty acid isopropyl ester with an iodine number of 63–73; and a $C_{16-18}$ fatty acid methyl ester with an iodine number of 70 to 80.

Sulfonation may be carried out in a known manner with sulfuric acid or oleum, 100 parts by weight of the mixture of (A) and (B) being reacted with from 10 to 20 parts by weight of the sulfonating agent with stirring and thorough cooling. The reaction products are homogeneous and readily stirrable until the reaction is completed. After any excess of sulfonating agent has been washed out, the products are neutralized with alkalis or ammonia and optionally bleached with $H_2O_2$.

It is of particular advantage to carry out sulfonation continuously with a mixture of $SO_3$ and air or inert gas, containing up to 8% by volume of $SO_3$, preferably 3–5%, most preferably 3.5–4.5%, in either a falling-film or cascade reactor. In this case, the reaction product remains fluid and homogeneous until sulfonation is over so that, even where fats containing relatively long-chain saturated or highly unsaturated fractions are used, the reactor remains free from blockage and the sulfonation product is not blackened or carbonized through excessively long contact times between the oil mixture and the mixture of $SO_3$ and air.

The reaction is carried out at temperatures of 20°–50° C., preferably 25°–45° C., and preferably with dissipation of the heat of reaction. Clear, relatively light-colored sulfonation products are obtained for high volume-time yields of the reactor. On completion of the reaction, the sulfonation products are neutralized with an alkali hydroxide, an ammonia solution or an amine and optionally bleached with $H_2O_2$. The desired degree of sulfonation of the products depends upon the purpose for which they are to be used and should be 3 to 30%, preferably 5 to 15%, by weight of organically bound sulfur trioxide.

The products obtained by the claimed process are readily employed as stuffing agents for leather and skins. They are used in a known manner as aqueous emulsions for fat-liquoring leather in a fat-liquoring effective quantity, preferably from 3 to 15% by weight of active substance, based on the pared weight of the leather, or for treating skins. The products are self-emulsifying, so that there is generally no need for emulsifiers to be added. To obtain special effects, they may be combined with at least one other standard leather treatment agent, such as non-sulfonated oils or fats including fish oil and neat's-foot oil, synthetic stuffing agents such as chloroparaffins, paraffin sulfonates, mineral oils or the like, or sulfited oils, such as fish oil sulfite. Optionally, they may be used in conjunction with anionic, nonionic or cationic emulsifiers, for example ethylene oxide adducts with higher fatty alcohols, alkyl phenols or fatty amines.

EXAMPLES 1. (A) 60% by weight of lard oil having an iodine number of 72, from which approximately 10% by volume of solids were separated at room temperature, and mixed at 60° C. with (B) 40% by weight of a $C_{10-20}$ fatty acid methyl ester having an iodine number of 70, to form a homogeneous, clear oil. The mixture was then continuously sulfonated at 25°–30° C. with a mixture of $SO_3$ and air in a ratio of 4.5:95.5 in a falling-film reactor run under normal conditions. The $SO_3$-content in the acidic ester, as determined by Epton's method, was approx. 6%. After neutralization of the acidic ester with concentrated ammonia at a temperature of 70° C., the product was bleached for 2 hours at 50° C. with 1% of a 30–35% $H_2O_2$ solution. The product was then adjusted to pH 8.0. The end product obtained, which was light, red-brown and liquid at room temperature, had a water content of approx. 22% and was readily emulsifiable in water.

2. A mixture of (A) 60% by weight of lard oil having an iodine number of 72, from which approx. 10% by volume of solids are separated at room temperature, and 40% by weight of a $C_{12-20}$ fatty acid isopropyl ester having an iodine number of 68 was sulfonated with 18% by weight of oleum (20% $SO_3$-content) based on the quantity of oil, in a stirrer-equipped vessel in a known manner at 30° to 33° C. and then washed. The $SO_3$-content in the acidic ester, as determined by Epton's method, was approx. 6%. The acidic ester was then neutralized to pH 8.0 with concentrated ammonia at a temperature of 60° C. The end product obtained, which was clear and red-brown in color, had a water content of approx. 23% and was readily emulsifiable in water.

3. In a falling-film reactor operated under normal conditions, a mixture of (A) 50% by weight of fish oil having an iodine number of 155 and (B) 50% by weight of a $C_{16-18}$ fatty acid methyl ester having a iodine number of 75 was continuously sulfonated at 40°–45° C. with a mixture of $SO_3$ and air in a ratio of 4.5:95.5 to an $SO_3$-content (Epton) in the acidic ester of 5.8%. After neutralization of the acidic ester with ammonia at a temperature of 70° C., the product was bleached for 3 hours at 50° C. with 1% of an approx. 30% hydrogen peroxide solution. The product was then adjusted to pH 8.0 with concentrated ammonia. The end product obtained, which was an oily liquid and red-brown at room temperature, had a water content of 25% and was readily emulsifiable in water.

4. Production of furniture leather

Test material: wet-blue, pared leather

| Operative Step | Amount (% by weight based on weight of leather) | Agent | Time (min.) |
|---|---|---|---|
| Washing: | 200 | water at 50° C. drain of water fresh water | 10 |
| Retanning: | 100 | water at 50° C. | 60 |
| | 3 | chrome tanning agent | |
| | 3 | 33% basic amphoteric synthetic tanning agent | |
| | 1.5 | Na—Al silicate rinse at 40° C. fresh liquor | |
| Neutralization | 100 | water at 40° C. | 60 |
| | 0.5 | masking neutralizing agent | |
| | 2 | Na bicarbonate wash at 60° C. | |
| Dyeing: | 100 | water at 60° C. | 10 |
| | 2 | neutral auxiliary tanning agent | |
| | 0.5 | ammonia | |
| | 3 | dye | 45 |
| Stuffing: | 8 | stuffing agent of Example 1 | emulsify 1:2 with water |
| | 4 | sulfited stuffing agent | |
| | 1.5 | $C_{12-18}$ fatty alcohol sulfate | 45 |
| | 1.5 | formic acid | 15 |
| | 1.5 | formic acid cold rinse leather to block further process as normal. | 30 |

5. Production of clothing-quality sheepskin napa

Test material: wet-blue sheepskins
% by weight, based on pared weight

| Operative Step | Amount (% by weight based on weight of leather) | Agent | Time (min.) |
|---|---|---|---|
| Washing: | 200 | water at 40° C. | 20 |
| | 1 | anionic surfactant fresh liquor | |
| Neutralization | 200 | water at 40° C. | 45 |
| | 2 | masking neutralizing agent rinse at 50° C. | |
| Tanning and Dyeing: | 200 | water at 50° C. | 10 |
| | 2 | neutral auxiliary tanning agent | |
| | 1 | ammonia | |
| | 3 | dye | 50 |

-continued

Test material: wet-blue sheepskins
% by weight, based on pared weight

| Operative Step | Amount (% by weight based on weight of leather) | Agent | Time (min.) |
| --- | --- | --- | --- |
| | 1 | formic acid | 30 |
| | 4 | resin tanning agent | 20 |
| | 4 | synthetic tanning agent | 45 |
| Stuffing: | 6 | stuffing agent of Example 3 | 45 |
| | 0.5 | complex-active emulsifier | |
| | 0.5 | formic acid cold rinse, hang-dry. | 30 |

6. Production of upper leather

Test material: wet-blue cowhide
% by weight, based on pared weight

| Operative Step | Amount (% by weight based on weight of leather) | Agent | Time (min.) |
| --- | --- | --- | --- |
| Washing: | 200 | water at 40° C. drain off liquor fresh liquor | 10 |
| Neutralization | 100 | water at 40° C. | 30 |
| | 1 | Na formate rinse at 60° C. fresh liquor | |
| Retanning | 100 | water at 60° C. | |
| | 1 | dye | 15 |
| | 2 | acrylate tanning agent | 15 |
| | 4 | synthetic tanning agent | 45 |
| Stuffing: | 4 | stuffing agent of Example 1 | emulsify 1:2 with water |
| | 2 | chloroparaffin sulfonate | |
| | 0.5 | complex-active emulsifier | 45 |
| | 0.5 | formic acid leather to block dry and further process as normal | 15 |

The leathers produced in Examples 4-6 all demonstrated satisfactory feel and other qualities and indicated that the stuffing agents of this invention were useful.

We claim:

1. A process for the sulfonation of a fat or oil containing unsaturated fractions consisting essentially of
   (1) sulfonating 100 parts by weight of a fat or oil mixture consisting of
      (A) 20 to 80% by weight of at least one $C_{8-24}$ fatty acid glycerol ester having an iodine number above 20, and
      (B) the balance q.s. to 100% by weight of at least one $C_{1-4}$ aliphatic monoalcohol ester of a $C_{8-24}$ fatty acid which is liquid at room temperature and has an iodine number of about 50-100, with about 10-20 parts by weight of sulfuric acid, oleum, or a mixture of $SO_3$ and air containing up to 8% by volume of $SO_3$, to a degree of sulfonation of about 3-30% by weight of organically bound sulfur trioxide;
   (2) neutralizing the resulting sulfonated fat or oil mixture with an alkali hydroxide, ammonia, or amine; and optionally
   (3) bleaching the neutralized sulfonated fat or oil mixture with a bleaching effective amount of $H_2O_2$.

2. The process of claim 1 wherein said component (A) consists essentially of at least one natural or synthetic $C_{16-24}$-fatty acid triglyceride having an iodine number of about 50-200.

3. The process of claim 1 wherein said component (A) consists essentially of at least one: natural $C_{16-24}$-fatty acid triglyceride mixture, or $C_{16-24}$-fatty acid triglyceride mixture produced from natural vegetable or animal fats; which fatty acids are partly mono- or polyunsaturated; said component (A) having an average iodine number of about 50-200.

4. The process of claim 1 wherein said component (A) consists essentially of: lard oil, neat's-foot oil, fish oil, rapeseed oil, peanut oil, olive oil, or any mixture thereof.

5. The process of claim 1 wherein said component (A) consists essentially of lard oil and/or fish oil.

6. The process of claim 1 wherein said component (B) consisting of at least one $C_{1-3}$-aliphatic monoalcohol ester of a $C_{12-20}$-fatty acid which is liquid and homogeneous at room temperature.

7. The process of claim 2 wherein said component (B) consisting of at least one $C_{1-3}$-aliphatic monoalcohol ester of a $C_{12-20}$-fatty acid which is liquid and homogeneous at room temperature.

8. The process of claim 1 wherein said component (B) consisting of at least one methyl or ethyl ester of a $C_{12-20}$-fatty acid having an iodine number of about 60-80.

9. The process of claim 3 wherein said component (B) consisting of at least one methyl or ethyl ester of a $C_{12-20}$-fatty acid having an iodine number of about 60-80.

10. The process of claim 1 wherein said component (B) consists essentially of: a $C_{12-18}$ fatty acid methyl ester having an iodine number of 60-70; a $C_{16-18}$ fatty acid ethyl ester having an iodine number of 60-70; a $C_{10-20}$ fatty acid methyl ester having an iodine number of 65-75; a $C_{12-20}$ fatty acid isopropyl ester having an iodine number of 63-73; a $C_{16-18}$ fatty acid methyl ester having an iodine number of 70-80; or any mixture thereof.

11. The process of claim 4 wherein said component (B) consists essentially of: a $C_{12-18}$ fatty acid methyl ester having an iodine number of 60-70; a $C_{16-18}$ fatty acid ethyl ester having an iodine number of 60-70; a $C_{10-20}$ fatty acid methyl ester having an iodine number of 65-75; a $C_{12-20}$ fatty acid isopropyl ester having an iodine number of 63-73; a $C_{16-18}$ fatty acid methyl ester having an iodine number of 70-80; or any mixture thereof.

12. The process of claim 1 wherein said component (B) consists essentially of: a $C_{10-20}$ fatty acid methyl ester having an iodine number of about 70; a $C_{12-20}$ fatty acid isopropyl ester having an iodine number of about 68; a $C_{16-18}$ fatty acid methyl ester having an iodine number of about 75; or any mixture thereof.

13. The process of claim 5 wherein said component (B) consists essentially of: a $C_{10-20}$ fatty acid methyl ester having an iodine number of about 70; a $C_{12-20}$ fatty acid isopropyl ester having an iodine number of about 68; a $C_{16-18}$ fatty acid methyl ester having an iodine number of about 75; or any mixture thereof.

14. The process of claim 1 wherein said component (A) is present in 50-70% by weight.

15. The process of claim 11 wherein said component (A) is present in 50-70% by weight.

16. The process of claim 13 wherein said component (A) is present in 50-70% by weight.

17. The process of claim 1 wherein: said sulfonation is conducted with a mixture of $SO_3$ and air containing up to 8% by volume of $SO_3$; is conducted at a temperature of about 20°-50° C.; and is conducted until the product thereof has an organically bound $SO_3$ content of about 3-30% by weight.

18. The process of claim 1 wherein: said sulfonation is conducted with a mixture of $SO_3$ and air containing about 3-5% by volume of $SO_3$; is conducted at a temperature of about 20°-50° C.; and is conducted until the product thereof has an organically bound $SO_3$ content of about 5-15% by weight.

19. The process of claim 15 wherein: said sulfonation is conducted with a mixture of $SO_3$ and air containing up to 8% by volume of $SO_3$; is conducted at a temperature of about 20°-50° C.; and is conducted until the product thereof has an organically bound $SO_3$ content of about 3-30% by weight.

20. The process of claim 19 wherein said reaction is conducted in a falling film or cascade reactor.

21. The process of claim 16 wherein: said sulfonation is conducted with a mixture of $SO_3$ and air containing about 3-5% by volume of $SO_3$; is conducted at a temperature of about 20°-50° C.; and is conducted until the product thereof has an organically bound $SO_3$ content of about 5-15% by weight.

22. The process of claim 21 wherein said reaction is conducted in a falling film reactor.

23. In a method for tanning leather wherein an aqueous fatliquoring composition is employed containing at least one stuffing agent in combination with at least one of: non-sulfonated natural oils and fats; synthetic stuffing agents based on chloroparaffins; paraffin sulfonates, mineral oils; sulfited oils; or anionic, nonionic, or cationic emulsifiers; the improvement consisting essentially of employing as said at least one stuffing agent the product of the process of claim 1.

24. In a method for tanning leather wherein an aqueous fatliquoring composition is employed containing at least one stuffing agent in combination with at least one of: non-sulfonated natural oils and fats; synthetic stuffing agents based on chloroparaffins; paraffin sulfonates, mineral oils; sulfited oils; or anionic, nonionic, or cationic emulsifiers; the improvement consisting essentially of employing as said at least one stuffing agent the product of the process of claim 11.

25. In a method for tanning leather wherein an aqueous fatliquoring composition is employed containing at least one stuffing agent in combination with at least one of: non-sulfonated natural oils and fats; synthetic stuffing agents based on chloroparaffins; paraffin sulfonates, mineral oils; sulfited oils; or anionic, nonionic, or cationic emulsifiers; the improvement consisting essentially of employing as said at least one stuffing agent the product of the process of claim 21.

* * * * *